United States Patent
Song

(10) Patent No.: US 9,270,032 B2
(45) Date of Patent: Feb. 23, 2016

(54) CONNECTOR WITH PIERCING TAIL

(71) Applicant: Molex, LLC, Lisle, IL (US)

(72) Inventor: Xiao Jun Song, Shanghai (CN)

(73) Assignee: Molex, LLC, Lisle, IL (US)

( * ) Notice: Subject to any disclaimer, the term of this patent is extended or adjusted under 35 U.S.C. 154(b) by 0 days.

(21) Appl. No.: 14/136,883

(22) Filed: Dec. 20, 2013

(65) Prior Publication Data

US 2014/0308850 A1    Oct. 16, 2014

(30) Foreign Application Priority Data

Dec. 26, 2012  (CN) .......................... 2012 1 0575967

(51) Int. Cl.
| | |
|---|---|
| *H01R 12/70* | (2011.01) |
| *H01R 4/24* | (2006.01) |
| *H01R 12/58* | (2011.01) |
| *A61N 1/05* | (2006.01) |
| *H01R 12/72* | (2011.01) |

(52) U.S. Cl.
CPC ............ *H01R 4/2404* (2013.01); *A61N 1/0502* (2013.01); *H01R 12/585* (2013.01); *H01R 12/724* (2013.01); *H01R 2201/12* (2013.01)

(58) Field of Classification Search
CPC .. H01R 12/7082; H01R 13/04; H01R 4/2404; H01R 12/585; H01R 2201/12; H01R 12/724; A61N 1/0502

USPC ........ 439/620.15, 884, 620.16, 387, 391, 444
See application file for complete search history.

(56) References Cited

U.S. PATENT DOCUMENTS

| | | | | |
|---|---|---|---|---|
| 3,699,498 | A | * | 10/1972 | Hardesty et al. .............. 439/248 |
| 4,054,350 | A | * | 10/1977 | Hardesty ........................ 439/418 |
| 4,258,469 | A | * | 3/1981 | Salvesen ......................... 29/884 |
| 4,685,466 | A | | 8/1987 | Rau |
| 4,837,049 | A | | 6/1989 | Byers et al. |
| 8,086,322 | B2 | | 12/2011 | Schouenborg |

\* cited by examiner

*Primary Examiner* — Edwin A. Leon
(74) *Attorney, Agent, or Firm* — Stephen L. Sheldon

(57) ABSTRACT

An electrical connector and a terminal thereof are provided. The electrical connector comprises a housing, a circuit board and a plurality of terminals. The housing comprises a body and an assembly frame. The body is formed with a first surface and a second surface which are opposite to each other, and includes a terminal mounting hole penetrating through the first surface and the second surface. The assembly frame extends outwardly from the second surface and forms a mounting surface. The circuit board is mounted to the mounting surface. The terminal comprises a main body, a plurality of pins and a pressing portion. The main body is mounted to the corresponding terminal mounting hole. The pins protrude out of the first surface from a side edge of the main body adjacent to the first surface.

13 Claims, 5 Drawing Sheets

CONNECTOR WITH PIERCING TAIL

RELATED APPLICATIONS

This application claims priority to Chinese Application No. 201210575967.3, filed Dec. 26, 2012, which is incorporated herein by reference in its entirety.

TECHNICAL FIELD

The present disclosure relates to an electrical connector and a terminal thereof, and particularly relates to an electrical connector and a terminal thereof for a needle-like electrode device.

BACKGROUND ART

Electrotherapy is a common therapeutic method in modern medicine. Using various currents having different frequencies to stimulate body tissues of patients can produce various medical effects including changing transfer function of peripheral nerve fibres, stimulating hormone secretion, and promoting tissue healing and the like. However, in various electrotherapy devices, a needle-like electrode medical device is often used to pierce into skin of a patient so as to perform a deeper and effective discharge treatment on the tissue of the patient. Moreover, the needle-like electrode can also be used for a medical detection.

An existing conventional technology, for example a U.S. Pat. No. 4,685,466 and a U.S. Pat. No. 8,086,322 (corresponding to a Chinese patent application No. CN200580042302.4), typically comprises a mounting and a plurality of needle-like electrodes fixed to the mounting. When the needle-like electrode device is manufactured, firstly the each needle-like electrode is inserted into the mounting one by one, then a plurality of conductors are respectively soldered to individual needle-like electrodes and a printed circuit board or a cable, finally, the each needle-like electrode and a medical device controlling current are electrically connected via the printed circuit board or the cable. Therefore, when the existing needle-like electrode device is manufactured, the each needle-like electrode not only is required to manufacture separately, but also needs a one-by-one inserting process on the mounting, then the each needle-like electrode and the corresponding conductor are soldered to each other. In the above manufacturing process, not only a highly precise positioning technology is need but also a manufacturing process is not easy, and the one-by-one inserting process results in a low manufacturing efficiency, meanwhile manufacturing cost is also increased; moreover, the elongated needle-like configuration needs a plurality of connections and adapters to be connected to the circuit board or the device, which also increases the manufacturing difficulty and the manufacturing cost. Therefore, the existing needle-like electrode device still has a room for improvement. Moreover, such the piercing invasive device is typically desired to be replaced and discarded after a disposable use, so the configuration needs to be more easily used, and needs to be cheaper.

SUMMARY OF THE INVENTION

A terminal includes a main body, a plurality of pins and a pressing portion. The main body comprises a first edge and a second edge which are provided at two opposite sides. The plurality of pins are spaced apart from each other and integrally extends outwardly from the first edge of the main body, and the each pin is a triangle and becomes a sharp angle at a distal end thereof. The pressing portion comprises an extension section integrally extending outwardly from the second edge of the main body, and a pressing section extending perpendicularly from the extension section.

An electrical connector comprises a housing, a circuit board and a plurality of terminals. The housing comprises a body and an assembly frame. The body is formed with a first surface and a second surface which are opposite to each other, and a plurality of terminal mounting holes penetrating through the first surface and the second surface. The assembly frame extends outwardly from the second surface and forms a mounting surface. The circuit board is mounted to the mounting surface of the assembly frame, and comprises a plurality of pressing holes penetrating through the circuit board, and a plurality of conductive traces connecting the plurality of pressing holes. The each terminal comprises a main body, a plurality of pins and a pressing portion. The each main body is mounted to the corresponding terminal mounting hole and has a first edge adjacent to the first surface and a second edge adjacent to the second surface. The each pin integrally extends outwardly from the first edge of the main body to protrude out of the first surface of the body. The pressing portion integrally extends outwardly from the second edge of the main body to protrude out of the second surface of the body, and at least part of the pressing portion protrudes out of the mounting surface of the assembly frame so as to be provided through the corresponding pressing hole to press against the circuit board and electrically connect with the plurality of conductive traces.

BRIEF DESCRIPTION OF THE DRAWINGS

The present invention is illustrated by way of example and not limited in the accompanying figures in which like reference numerals indicate similar elements and in which.

DETAILED DESCRIPTION OF THE PREFERRED EMBODIMENTS

Figure 1:
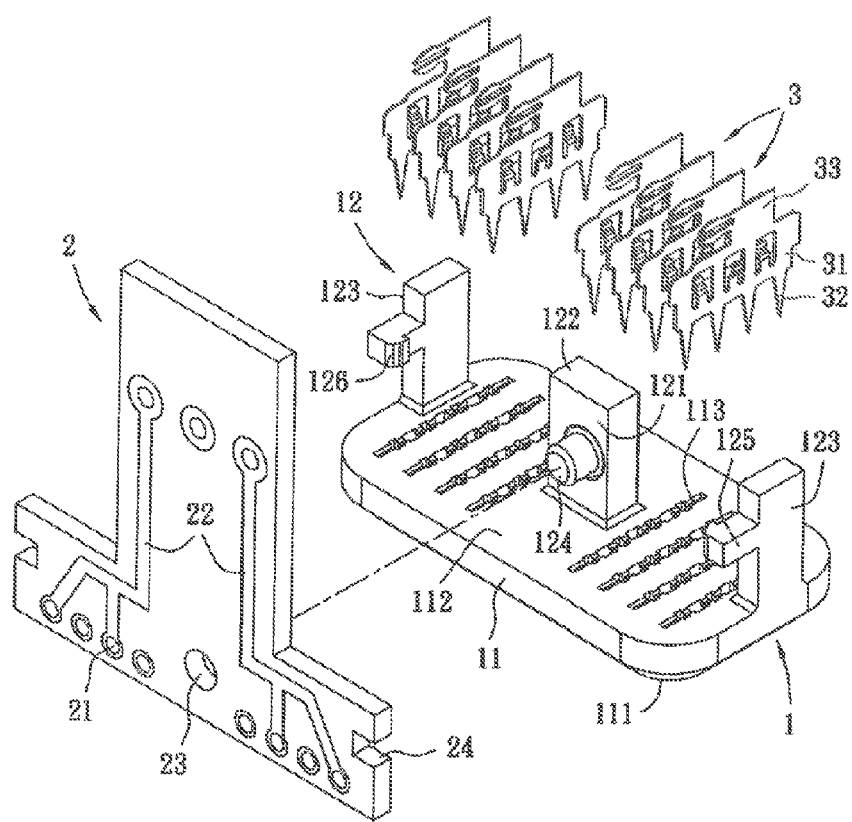
FIG. 1 is an exploded perspective view illustrating an embodiment of an electrical connector.
Figure 2:
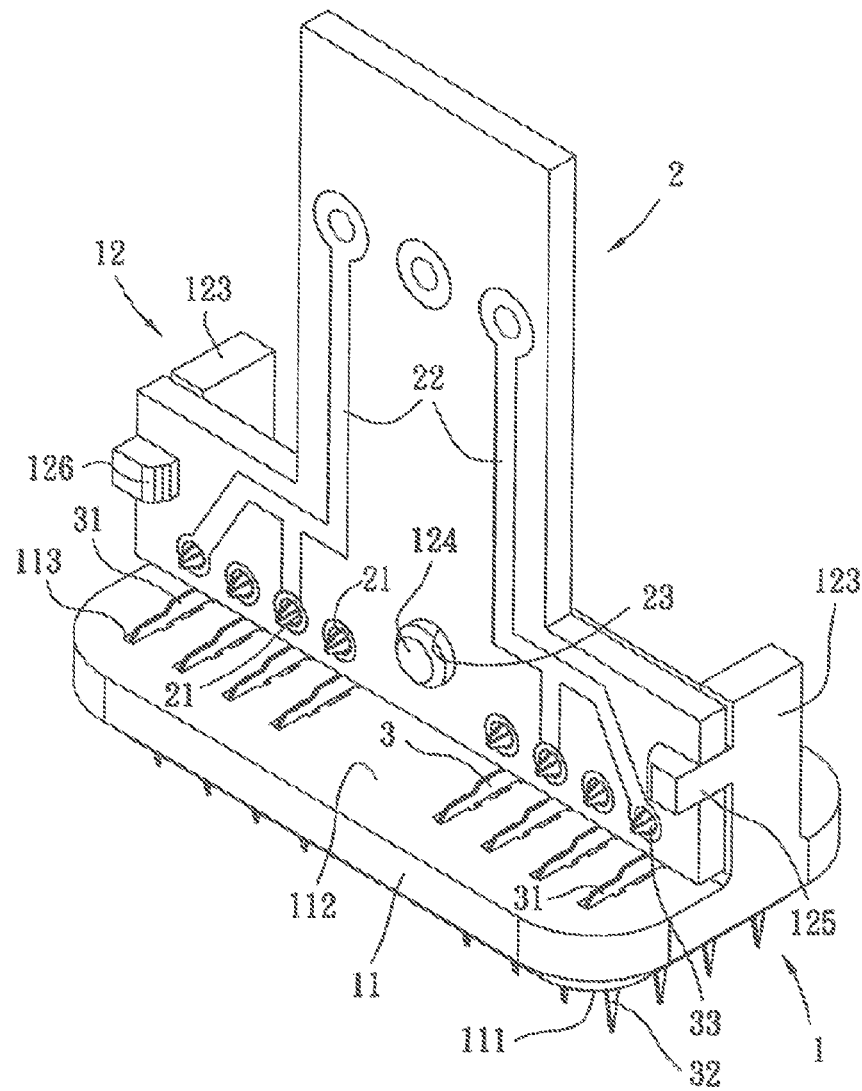
FIG. 2 is a perspective view illustrating an assembling manner of the embodiment.
Figure 3:
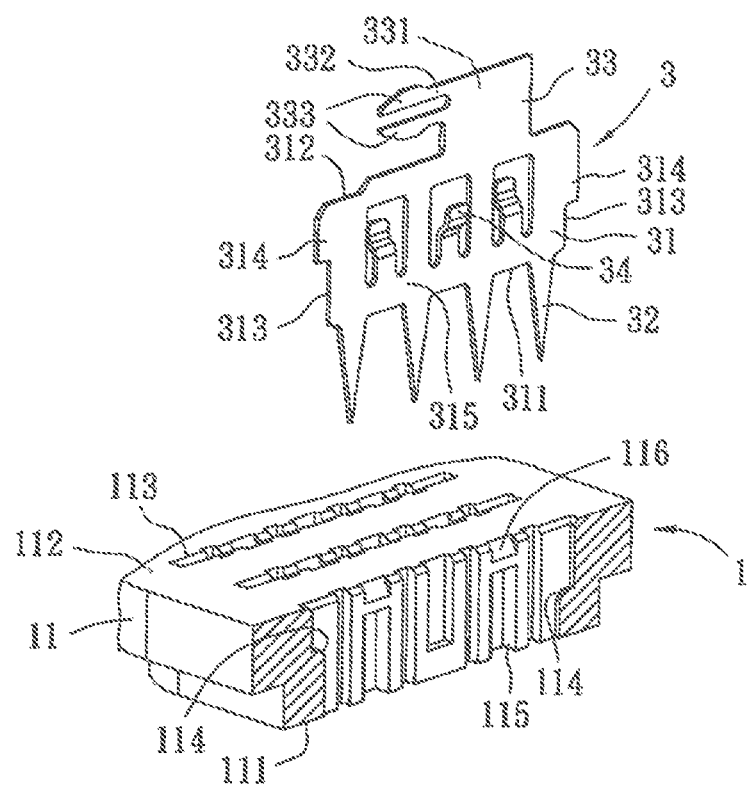
FIG. 3 is a partial cut away view illustrating configurations of a terminal and a terminal mounting hole of the embodiment.
Figure 4:
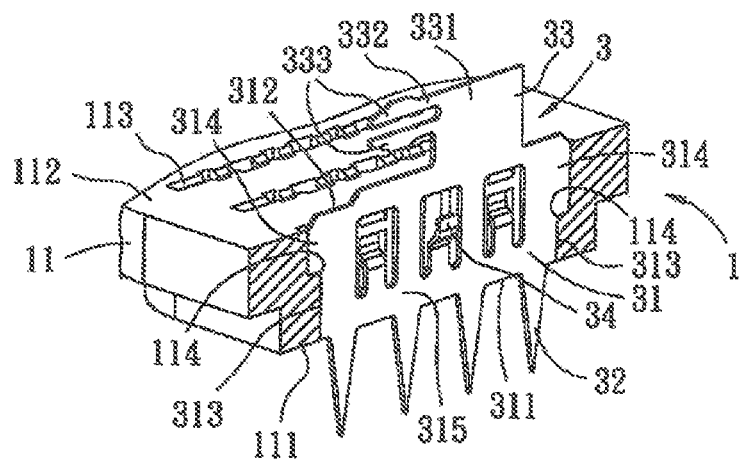
FIG. 4 is a view similar to FIG. 3 illustrating assembling of the terminal and the terminal mounting hole of the embodiment.
Figure 5:
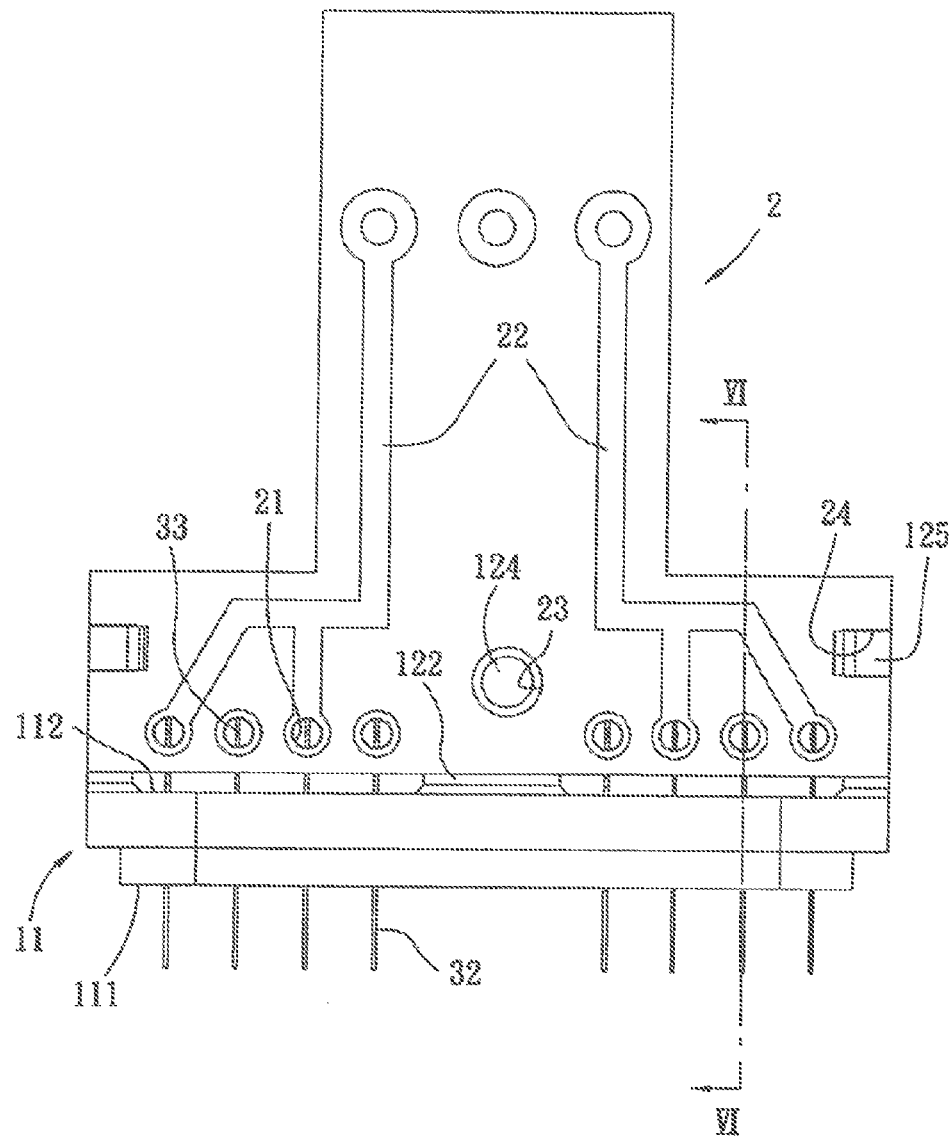
FIG. 5 is a side view illustrating a circuit board of the embodiment.

The foregoing and other technical contents, features and effects of the present disclosure will be apparent through the following detailed description for a specific embodiment in combination with the drawings.

As can be appreciated, one benefit of the disclosure is the ability to provide a terminal which has a plurality of pins integrally formed so that manufacture is quick. Another benefit is the ability to provide an electrical connector which has the aforementioned terminal and is easily assembled and is low in cost.

As depicted, the terminal comprises the plurality of pins and a pressing portion pressing against the circuit board which are integrally formed with the main body, the pins are directly electrically connected with the circuit board via the pressing portion, and thus can be connected with the conductive traces of the circuit board without any additional connecting conductors, which improves manufacturability. Moreover, since the pins and the pressing portion are integrally formed to the terminal, thereby the pins and the pressing portion can be directly formed stamping a metal sheet so as to be quickly and manufactured in a great quantity and avoid the time-consuming manufacturing process of separately manufacturing the each pin. And the design that the plurality of pins are directly formed to the terminal avoids the need to insert the pins one by one in the housing, instead one can just insert the terminal into the terminal mounting hole, thereby considerably reducing the manufacturing difficulty in securing the pins to the housing.

Referring to FIGS. 1-4, an electrical connector of an embodiment of the present disclosure is illustrated, the electrical connector comprises a housing 1 (formed of an insulative material), a circuit board 2 and terminals 3 (as depicted, eight terminals). The housing 1 comprises a body 11 and an assembly frame 12. The body 11 is formed with a first surface 111 and a second surface 112 which are opposite to each other, and terminal mounting holes 113 penetrating through the first surface 111 and the second surface 112. The assembly frame 12 extends outwardly from the second surface 112 of the body 11 to form a mounting surface 121 which is perpendicular to the second surface 112, and has a middle portion 122 and two clamp portions 123 spaced apart and provided respectively at two opposite sides of the middle portion 122.

The circuit board 2 is mounted to the mounting surface 121 of the assembly frame 12, and comprises a plurality of pressing holes 21 penetrating through the circuit board 2, a plurality of conductive traces 22 connecting the plurality of pressing holes 21, a positioning hole 23 penetrating through the circuit board 2, and two notches 24 respectively formed at two opposite sides of the circuit board 2. The middle portion 122 of the assembly frame 12 has a positioning post 124 protruding from the mounting surface 121 and provided through the positioning hole 23; the two clamp portions 123 of the assembly frame 12 protrude from the mounting surface 121 and is formed with two hooks 125 corresponding to the two notches 24 of the circuit board 2 in position; distal ends of the hooks 125 is bent inwardly to latch on the corresponding notches 24. Distal ends of inner sides of the two hooks 125 each form a guide surface 126 to allow that the two hooks 125 to smoothly engage and latch to the notches 24 when the circuit board 2 and the assembly frame 12 are assembled. In operation, the positioning post 124 of the assembly frame 12 is positioned into the positioning hole 23 of the circuit board 2 and the two hooks 125 and the notches 24 are latched so as to secure the two opposite sides of the circuit board 2. As can be appreciated, the assembly frame 12 helps to securely support the circuit board 2 when the circuit board 2 assembled and fixed to the mounting surface 121 of the assembly frame 12. Sides of the pressing hole 21 are provided with a conductive plating layer to be electrically connected with the conductive trace 22.

Figure 6:
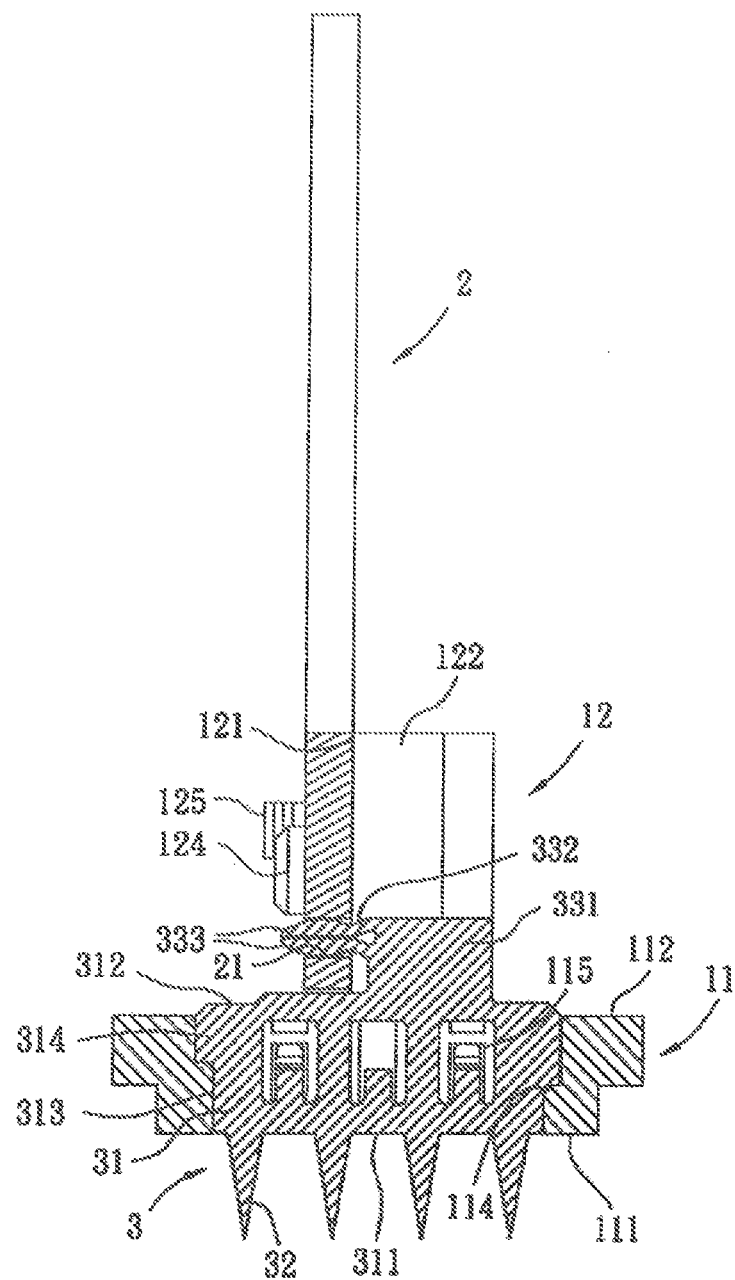
FIG. 6 is a cross-sectional view taken along a line VI-VI of FIG. 5 illustrating the assembling manner of the terminal and the terminal mounting hole of the embodiment.

Each terminal 3 can be formed by stamping a stainless steel piece with a mold, and comprises a main body 31, four pins 32 and a pressing portion 33. The main body 31 is mounted to the corresponding terminal mounting hole 113 of the body 11 of the housing 1, and has a first edge 311 and a second edge 312 provided at opposite sides, two third edges 313 each connecting the first edge 311 and the second edge 312 with two ends thereof, and two surfaces 315 respectively positioned at opposite sides of the main body 31. The first edge 311 is adjacent to the first surface 111, the second edge 312 is adjacent to the second surface 112. Each pin 32 integrally extends outwardly from the first edge 311 of the main body 31 and protrudes out of the first surface 111 of the body 11, and is a rough triangle and becomes a sharp angle at a distal end thereof. The triangular shape of the pin 32 makes a connecting area between the pin 32 and the main body 31 larger, which improves the structure strength of the connecting area between the pin 32 and the main body 31 and reduces the potential for damage while improving manufacturability. The pressing portion 33 integrally extends outwardly from the second edge 312 of the main body 31 and protrudes out of the second surface 112 of the body 11 and has an extension section 331 extending outwardly from the second edge 312 and a pressing section 332 extending perpendicularly from the extension section 331. The pressing section 332 has two legs 333 which are spaced apart from each other and protrude out of the mounting surface 121. The two legs 333 are provided through the corresponding pressing holes 21 to connect with the circuit board 2 in pressing fit, and are limited and pressed by the circuit board 2 in the pressing hole 21 to become slightly closer to each other (referring to FIG. 6) and press against the hole-walls of the pressing holes 21, thereby making the terminal 3 and the conductive trace 22 of the circuit board 2 electrically connected.

Referring to FIGS. 3-6, the body 11 of the housing 1 is recessed in each terminal mounting hole 113 and provides two step portions 114 that respectively correspond to the two third edges 313 of the terminal 3, and three latching grooves 115 which are corresponding to the surface 315 of the terminal 3. The main body 31 of the each terminal 3 further comprises two shoulders 314 which respectively protrude outwardly from the two third edges 313 to respectively abut against the step portions 114, and the each terminal 3 further comprises three latching tabs 34 which are formed to the main body 31 and distal ends of which each protrude out of one of the surfaces 315 of the main body 31. The three latching tabs 34 respectively extend into the corresponding latching grooves 115 and are fixedly received in the corresponding latching grooves 115. As the shoulders 314 abut against the step portions 114 of the housing 1, the main body 31 are limited relative to the housing 1 in a direction of moving toward the first surface 111; and by that the each latching tab 34 is received and fixed in the latching groove 115 of the housing 1, the main body 31 is limited relative to the housing 1 in a direction of moving toward the second surface 112. By the engagements of the shoulders 314, the step portions 114, the latching tabs 34 and the latching grooves 115 therebetween, the main body 31 is limited from moving relative to the housing 1 in the directions perpendicular to the first surface 111 and thus the main body 31 is reliably fixed to the terminal mounting hole 113.

In the embodiment, the latching tabs 34 of the each terminal 3 are spaced apart from each other and arranged side-by-side in the main body 31, and alternately protrude out of the two opposite surfaces 315 of the main body 31 toward opposite directions, by that the plurality of latching tabs 34 are cooperated, the each main body 31 is limited by the latching grooves 115 of the housing 1 on the two opposite surfaces 315, which gives the each terminal 3 a more stable fixing effect. As the body 11 is formed with a slope 116 at a location between the second surface 112 and the each latching groove 115 in the terminal mounting hole 113, the latching tabs 34 may be smoothly guided into the corresponding latching groove 115 by the slope 116 when the each terminal 3 is inserted into the terminal mounting hole 113. Furthermore, distances between the two shoulders 314 of the each terminal 3 and the first edge 311 are not identical, and distances between positions of the two step portions 114 in the each terminal mounting hole 113 of the housing 1 where the corresponding shoulders 314 are engaged with the two step portions 114 respectively and the first surface 111 are not identical, that is there is a corresponding height difference between the two shoulders 314 and there is a corresponding height difference between the two step portions 114, so that the two shoulders 314 and the two step portions 114 are compatible only in a single direction. This configuration provides a polarizing mechanism when the terminal 3 is inserted into the terminal mounting hole 113 and helps ensure the terminal 3 is inserted and fixed to the terminal mounting hole 113 in a correct direction and would not be incorrectly inserted. In an embodiment, the pressing section 332 of the terminal 3 can use, for example, a needle eye shaped pressing configuration.

Furthermore, in order to increase the fixing effect of the circuit board 2 and the housing 1, a distal end of the positioning post 124 formed at the middle portion 122 of the housing 1 passes through the circuit board 2, and a part of the positioning post 124 protruding out of the positioning hole 23 is hot melt so as to be connected with and be fixed to the circuit board 2, thereby making the positioning post 124 produce a better fixing effect similar to that an rivet does. Moreover, in the embodiment, after the pressing portion 33 of the terminal 3 is inserted into the pressing hole 21 of the each circuit board 2, the pressing hole 21 of the each circuit board 2 is filled with conductive epoxy, which contacts the pressing portion 33 and the circuit board 2, thereby not only improving fixity between the pressing portion 33 and the circuit board 2, but also helps improve the electrical connection between the pressing portion 33 and the circuit board 2.

As can be appreciated, therefore, in an embodiment the plurality of pins 32 are integrally protruded from the first edge 311 of the main body 31 of the terminal 3, the individual pins 32 do not need to be separately manufactured, and may be formed by stamping a metal piece with directly cooperating the manufacturing of the terminal 3, thereby reaching an effect of a quick and high manufacture. In addition, the main body 31 of the terminal 3 and the housing 1 can be fixed to each other by inserting the pins 32 into the housing 1 without the need to individually stich each pin in a heavy and repeating manner, thereby considerably reducing the manufacturing difficulty. Moreover, the terminal 3 is integrally protruded outwardly from the second edge 312 of the main body 31 to form the pressing portion 33, and the pressing portion 33 presses against the circuit board 2 by that the pressing portion 33 is inserted into the pressing hole 21, thus assembling the terminal 3 and the circuit board 2 is easy and quick. And, as can be appreciated, the electrical connections between the pins 32 of the terminal 3 and the conductive traces 22 of the circuit board 2 can completed without any additional connecting conductors.

What have been described above are only embodiments of the present disclosure, the implementation scope of the present disclosure is not limited to that, that is, simple equivalent variations and modifications made according to the Claims and the description content of the present disclosure are still included in the protective scope of the present disclosure.

What is claimed is:

1. An electrical connector, comprising:
a housing with a body and an assembly frame, the body having a first surface and a second surface which are opposite to each other, and a plurality of terminal mounting holes penetrating through the first surface and the second surface, the assembly frame extending outwardly from the second surface and forming a mounting surface;
a circuit board mounted to the mounting surface of the assembly frame and including a plurality of pressing holes that penetrate through the circuit board, and a plurality of conductive traces connecting the plurality of pressing holes; and
a plurality of terminals, each of the plurality of terminals having a main body, a plurality of pins and a pressing portion, the main body being mounted to the corresponding terminal mounting hole and having a first edge adjacent to the first surface and a second edge adjacent to the second surface, the plurality of pins integrally extending outwardly from the first edge of the main body to protrude out of the first surface of the body, the pressing portion integrally extending outwardly from the second edge of the main body to protrude out of the second surface of the body, and at least part of the pressing portion protruding out of the mounting surface of the assembly frame so as to be provided through the corresponding pressing hole to press against the circuit board and electrically connect with the plurality of conductive traces.

2. The electrical connector according to claim 1, wherein the each pin is triangular shaped and extends outwardly from the first edge and forms a sharp angle at a distal end thereof.

3. The electrical connector according to claim 1, wherein the mounting surface of the assembly frame is perpendicular to the second surface of the body; the pressing portion has an extension section extending outwardly from the second edge of the main body, and a pressing section extending perpendicularly from the extension section.

4. The electrical connector according to claim 3, wherein the pressing section has two legs spaced apart from each other.

5. The electrical connector according to claim 1, wherein the main body of the each terminal further comprises two third edges each connecting with the first edge and the second edge respectively with two ends thereof, two shoulders formed by protruding outwardly respectively from the two third edges, and two surfaces which are positioned at two opposite sides; the each terminal further comprises a plurality of latching tabs which are formed to the main body and distal ends of the plurality of latching tabs each protrude out of one of the surfaces of the main body; the body is formed with a plurality of latching grooves in the terminal mounting hole to respectively receive and limit the plurality of latching tabs, and two step portions respectively provided for the two shoulders to abut against.

6. The electrical connector according to claim 5, wherein the plurality of latching tabs are spaced apart from each other and arranged side by side, and alternately protrude out of the two surfaces of the main body toward opposite directions.

7. The electrical connector according to claim 5, wherein respective distances between the two shoulders of the each terminal and the first edge are not identical, the two step portions corresponding to the two shoulders in position, and respective distances between the two step portions and the first surface are not identical.

8. The electrical connector according to claim 1, wherein the circuit board further comprises a positioning hole penetrating through the circuit board, and two notches formed at two opposite sides of the circuit board; the assembly frame has a middle portion, and two clamp portions spaced apart and provided respectively at the two opposite sides of the middle portion; the middle portion has a positioning post provided through the positioning hole; the two clamp portions are formed with two hooks respectively latching on the two notches to clip the circuit board cooperatively.

9. The electrical connector according to claim 8, wherein a distal end of the positioning post protrudes out of the positioning hole, and a part of the positioning post protruding out of the positioning hole is hot melt to connect with and be fixed to the circuit board.

10. The electrical connector according to claim 1, wherein the pressing hole of the each circuit board therein is filled with conductive epoxy that contacts the pressing portion and the circuit board.

11. The electrical connector according to claim 1, wherein the plurality of pins extending outwardly from the first edge comprised by the each terminal are provided as four in number.

12. An electrical connector, comprising:
a housing with a body and an assembly frame, the body having a first surface and a second surface which are opposite to each other, and a plurality of terminal mounting holes penetrating through the first surface and the second surface, the assembly frame extending outwardly from the second surface and forming a mounting surface;
a circuit board mounted to the mounting surface of the assembly frame including a plurality of conductive traces; and
a plurality of terminals mounted in the housing, each of the plurality of terminals having a main body supported by the housing and a plurality of pins extending out of the first surface of the body, each of the terminals electrically connected to one of the plurality of traces, wherein the plurality of pins are triangular shaped.

13. The electrical connector of claim 12, wherein the circuit board is aligned in a first direction so that one of its surfaces forms an imaginary plane and the plurality of pins of each terminal are aligned in a second direction that is substantially perpendicular to the imaginary plane.

* * * * *